United States Patent [19]

von Weissenfluh

[11] Patent Number: 4,500,288

[45] Date of Patent: Feb. 19, 1985

[54] ANGULAR MOLD FOR DENTAL USE

[75] Inventor: Hans C. von Weissenfluh, Magadino, Switzerland

[73] Assignee: Hawe-Neos Dental Dr. H. v. Weissenfluh S.A., Gentilino, Switzerland

[21] Appl. No.: 454,851

[22] Filed: Dec. 30, 1982

[30] Foreign Application Priority Data

Jan. 21, 1982 [CH] Switzerland .......................... 350/82

[51] Int. Cl.$^3$ .............................................. A61C 9/00
[52] U.S. Cl. ...................................... 433/40; 433/39; 433/48
[58] Field of Search .............. 433/39, 40, 37, 38, 433/41, 44, 45, 46, 47, 48, 149, 226

[56] References Cited

U.S. PATENT DOCUMENTS

| | | | |
|---|---|---|---|
| 1,265,581 | 5/1918 | Zurbrigg | 433/39 |
| 1,778,293 | 10/1930 | Galasso | 433/37 |
| 2,607,117 | 8/1952 | Baughan | 433/39 |
| 2,629,172 | 2/1953 | Keiger | 433/40 |
| 3,064,354 | 11/1962 | Pos | 433/71 |
| 3,082,531 | 3/1963 | Jacobson | 433/39 |
| 3,736,663 | 6/1973 | White | 433/38 |

FOREIGN PATENT DOCUMENTS 2250507  6/1975  France ................................ 433/37

*Primary Examiner*—John J. Wilson
*Attorney, Agent, or Firm*—Young & Thompson

[57] ABSTRACT

The mold in question includes a cap (1) of transparent material strengthened by a single or multiple reinforcement (2, 2', 3) of wire or metal strip incorporated in the plastic of the cap. The cap (1) or reinforcement ends above in a stem (1') which makes it possible to grasp the mold and hold it in place for the entire time of polymerization of the filling mastic performed by ultraviolet or visible light rays. This mold is particularly suited for giving the exact shape of the filling of front teeth, both on the right and left side.

14 Claims, 9 Drawing Figures

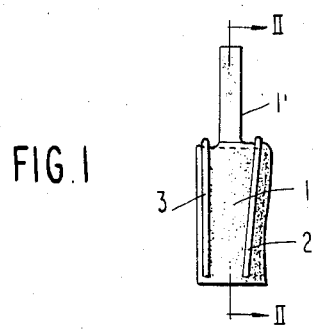
FIG.1
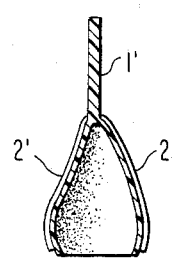
FIG.2
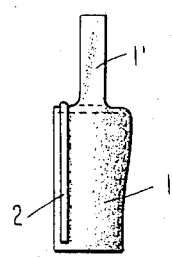
FIG.3
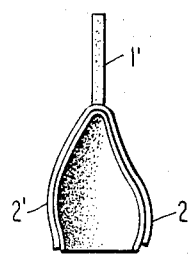
FIG.4
FIG.5
FIG.6
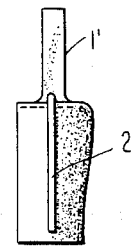
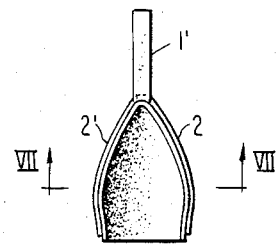
FIG.7
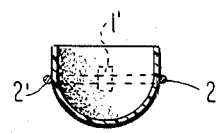
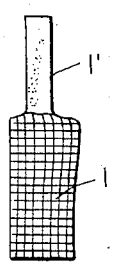
FIG.8
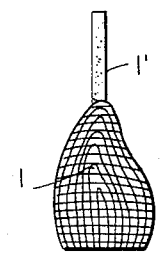
FIG.9

ANGULAR MOLD FOR DENTAL USE

This invention has as its object an angular mold for dental use comprising a cap of material transparent to ultraviolet rays and the rays of the visible solar spectrum to allow rapid hardening of the filling mastic by polymerization and a material that does not adhere to said filling mastic.

It is used in particular to give the exact shape to the filling of front teeth and is called "angular" because it fits the filling made at the end of the front teeth on the right or left mesial or distal side, i.e., at an angle.

Angular molds are known for filling of incisors comprising a metal cap that is forced on the tooth before applying the mastic to take the desired shape.

If the known cap is transparent, made of elastic material, it is possible to use mastics that can be polymerized by ultraviolet and visible rays, but the cap itself only approximately gives the final shape to the filling since it is not easily deformable.

This known type of transparent cap is actually preshaped (so that the mold gives shape to the tooth) and are made of elastic material and can be cut in half lengthwise to obtain two caps, one right and the other left.

The mold according to the invention differs from the latter known types by the fact that it is strengthened with reinforcement that takes the shape of the tooth, and the cap or reinforcement is provided with a stem that allows the mold to be grasped without blocking the passage of the rays that cause polymerization of the mastic.

For better understanding, the accompanying drawings represent some preferred embodiments of the mold in question.

FIG. 1 represents a first embodiment in side view in which the mold is provided with a reinforcement made up of two metal forks, one front, the other back.

FIG. 2 represents the corresponding cross section made along the plane going through II—II of FIG. 1.

FIG. 3 represents another embodiment with the reinforcement made by a single front fork, whose shape is indicated in FIG. 4.

FIG. 5 represents a further variant in which the reinforcement consists of a central metal fork.

FIG. 6 represents a lengthwise section.

FIG. 7 the crosswise section made along the plane going through VII—VII of FIG. 6; and, FIGS. 8 and 9 are views similar to FIGS. 1 and 2, respectively, but of a further variant in which the reinforcement comprises a metal net.

With reference to the various figures, the mold consists of a cap 1 of transparent plastic (for example, polymethylpentene, polycarbonate, polyvinyl chloride, polyester, etc.) ending in the upper part in a stem that allows the mold to be grasped while avoiding blocking the ultraviolet or visible rays which, by going through cap 1, reach the filling mastic and polymerize it.

According to the invention, cap 1 is strengthened by a reinforcement consisting in this case of two forks 2 and 3 of metal wire or metal strap.

Fork 3 is located at the front of cap 1, i.e., close to its opening, and fork 2 is located in the vicinity of the base of the cap.

FIG. 2 shows the progression of the two prongs 2, 2' of fork 2 which reproduces the shape of the front tooth to be filled.

Forks 2 and 3 are of metal wire to assume, by compression, the exact shape of the tooth to be filled.

FIGS. 3 and 4 represent a variant whereby the reinforcement consists of a single front fork 2 and has a progression opposite that shown in FIG. 2 because it is used to cover the filling on the opposite side of the tooth with respect to that of FIG. 2.

In other words, if the mold of FIG. 2 were used to cover the filling made on the left side of an incisor, the mold of FIG. 4 is used to cover the filling made on the right side of the same tooth.

FIGS. 5, 6 and 7 show a further variant in which fork 2 consists of a central fork and has a shape so as to cover a filling either on the right or left side of the tooth.

Preferably the reinforcement is buried in the transparent plastic of the cap and it is not ruled out for it to be able to form upper stem 1' which makes it possible to grasp the mold and mold it in place during the initial phase of polymerization of the mold.

As shown in FIGS. 8 and 9, the reinforcement can further be strengthened or replaced by a metallic or nonmetallic net embedded in the transparent plastic of the cap or by a metallic or nonmetallic sheet with small holes to fit the anatomical shape of the tooth, all this always within the scope of the invention.

What is claimed is:

1. An angular mold for dental use comprising a cap of material transparent to ultraviolet rays and the rays of the visible solar spectrum, the cap having the shape of the lateral half of a human tooth and being open on one side and closed at its top and open at its bottom, the cap having a stem on its closed top that makes it possible to grasp the mold without blocking the passage of the rays of ultraviolet and visible light, and a permanently deformable reinforcement that extends from top to bottom of the cap and that occupies only a minor portion of the area of the cap thereby to avoid blocking said rays.

2. Mold as in claim 1, wherein the reinforcement is metallic.

3. Mold as in claim 1, wherein said reinforcement is fork-shaped with a V progression (2, 2') and buried in the transparent plastic or the cap (1), a transparent material that extends into a handle (1').

4. Mold as in claim 3, wherein said V reinforcement has branches which are shaped to fit the profile of the tooth to be filled.

5. Mold as in claim 4, wherein said reinforcement consists of a fork located forward with respect to the cap, i.e., in the vicinity of its side opening.

6. Mold as in claim 4, wherein said cap has a center line opposite said side opening and said reinforcement consists of a fork located along said center line of said cap.

7. Mold as in claim 4, wherein said reinforcement consists of a fork located at the bottom of said cap.

8. Mold as in claim 4, wherein said reinforcement consists of two forks with one located at the side opening, the other at the bottom of said cap.

9. Mold as in claim 4, wherein said reinforcement is shaped to be inserted on either side of the tooth to be filled.

10. Mold as in claim 4, wherein said reinforcement is symmetrical, to enable it to be inserted on either side of the tooth to be filled.

11. Mold as in claim 1, wherein said reinforcement is plastic.

12. Mold as in claim 1, wherein said fork is of a metallic material permanently deformable by crushing against the tooth to be filled.

13. Mold as in claim 1, wherein said reinforcement consists of a net embedded in the transparent material of the cap.

14. Mold as in claim 1, wherein said reinforcement is a metallic net.

* * * * *